United States Patent [19]

Grollier

[11] Patent Number: 4,904,275

[45] Date of Patent: Feb. 27, 1990

[54] HAIR DYEING COMPOSITION BASED ON OXIDATION DYES AND BIO-HETEROPOLYSACCHARIDES

[75] Inventor: Jean F. Grollier, Paris, France

[73] Assignee: L'oreal, Paris, France

[21] Appl. No.: 132,652

[22] Filed: Dec. 10, 1987

Related U.S. Application Data

[63] Continuation of Ser. No. 811,763, Dec. 20, 1985, abandoned.

[30] Foreign Application Priority Data

Dec. 21, 1984 [LU] Luxembourg ............................ 85705

[51] Int. Cl.$^4$ ............................ A61K 7/13; C08L 5/00
[52] U.S. Cl. ............................................ 8/408; 8/406; 8/410; 8/411; 8/412; 8/416; 8/421; 8/423; 8/424
[58] Field of Search .................... 8/406, 408, 410, 411, 8/412, 416, 421, 423, 424

[56] References Cited

U.S. PATENT DOCUMENTS

| | | | |
|---|---|---|---|
| 3,884,627 | 5/1975 | Brody et al. | 8/411 |
| 4,092,102 | 5/1978 | Halasz et al. | 8/411 |
| 4,323,360 | 4/1982 | Bugaut et al. | 8/411 |

FOREIGN PATENT DOCUMENTS

| | | |
|---|---|---|
| 0113418 | 7/1984 | European Pat. Off. . |
| 2132627 | 7/1984 | United Kingdom . |
| 2142348 | 1/1985 | United Kingdom . |
| 2142920 | 1/1985 | United Kingdom . |

*Primary Examiner*—Paul Lieberman
*Assistant Examiner*—Linda D. Skaling
*Attorney, Agent, or Firm*—Fleit, Jacobson, Cohn, Price, Holman & Stern

[57] ABSTRACT

The invention relates to a dyeing composition for keratinous fibres, and especially for human hair, containing at least one oxidation dye precursor and at least one water-soluble bio-heteropolysaccharide in a cosmetically acceptable medium, and not containing an oxidizing agent with develops the oxidation dye precursors.

12 Claims, No Drawings

HAIR DYEING COMPOSITION BASED ON OXIDATION DYES AND BIO-HETEROPOLYSACCHARIDES

This application is a continuation of application Ser. No. 811,763, filed Dec. 20, 1985, now abandoned.

The present invention relates to dyeing compositions for keratinous fibres, especially for colouring human hair, based on oxidation dyes and compositions not containing an oxidizing agent and being intended to be mixed at the time of use with a composition containing oxidizing agents.

The colouring of keratinous fibers such as human hair can be accomplished either using so-called "direct" dyes capable in themselves of colouring the keratinous fibres, or alternatively by so-called "oxidation" dyes which, after their dyeing power has been developed in an oxidizing medium, enable a coloration to be obtained which is resistant to several applications of shampoo, to light and to adverse weather conditions.

Oxidation dyes are generally not dyes in themselves but are intermediate compounds, initially having little or no colour, commonly known as "precursors or oxidation bases" which develop their dyeing power in an oxidizing medium, generally consisting of hydrogen peroxide, to give rise to a dye in basic medium according to a process of oxidative condensation, either of the oxidation dye precursor with itself or of the "oxidation precursor or base" with a compound known as a modifier or coupler.

The variety of molecules introduced which consist of "oxidation bases" and couplers enables a rich selection of colourings to be obtained in the range of natural, black and ashen shades, and shades showing glints.

The so-called "permanent" dyeing obtained by means of these oxidation dyes has, moreover, to satisfy a number of requirements: it must have no drawback from the toxicological standpoint, must enable shades to be obtained of the desired intensity and must show good stability to external agents (light, adverse weather conditions, washing, permanent waving, acidic or basic perspiration, and friction).

The dyes must also enable white hair to be masked and must be as unselective as possible, that is to say show the least possible variation in coloration along the hair fibre, which can be sensitized to different extents between the ends and the roots.

In consequence of the large number of requirements, "oxidation base/coupler" combinations have not hitherto been completely satisfactory.

The Applicant has now discovered that, surprisingly, by introducing a certain amount of a bio-heteropolysaccharide into the composition containing the oxidation dyes, but not containing an oxidizing agent, it is possible, after applying the composition with an oxidizing agent on natural or permanently-waved hair, to improve the fastness of the shades to light and to washing, to intensify these shades or to improve their reproducibility at the desired intensity, and especially for hot shades showing glints, such as red and coppery shades.

Furthermore, the dyeing compositions show improved covering of white hair and a decrease in selectivity.

The presence of a bio-heteropolysaccharide in the composition containing the oxidation dyes, but not containing an oxidizing agent, enables, in addition, better preservation of the oxidation dye precursors to be achieved, by avoiding destabilization of the emulsion containing these dyes at the storage temperatures of hairdressing salons (20°–45° C.) and/or oxidation of these dyes.

The subject of the present invention is hence new dyeing compositions for the permanent or oxidation dyeing of keratinous fibres, especially human hair, containing at least one oxidation dye precursor and at least one bioheteropolysaccharide, this composition not containing the oxidizing agents which are intended for developing the colouring on the hair.

The subject of the invention is also the use of these compositions for dyeing keratinous fibres, especially human hair.

Other subjects of the invention will emerge on reading the description of the examples which follow.

The dyeing composition intended for use for oxidation dyeing of keratinous fibres, especially human hair, is mainly characterized in that it comprises at least one oxidation dye precursor and at least one water-soluble bio-heteropolysaccharide, which is a water-soluble heteropolysaccharide in a cosmetically acceptable medium not containing an oxidizing agent for developing the coloration on the hair.

The oxidation dye precursors used in the dyeing composition according to the invention are chosen from oxidation dye precursors of the para or ortho type, such as para-phenylenediamines, para-aminophenols, para-diphenols, ortho-aminophenols, ortho-phenylenediamines, ortho-diphenols and heterocyclic oxidation dye precursors chosen from pyrindin or pyrimidin derivatives. These compositions are known per se and can optionally be substituted on the amine groups or on the benzene or heterocyclic rings with alkyl, hydroxyalkyl, halogen or alkoxy groups, or amine groups optionally substituted with alkyl or hydroxyalkyl groups.

For precursors of the para type which can be used according to the invention, reference should be made to French Patent 2,421,607.

Among these compounds, there may be mentioned, more especially, para-phenylenediamine, 2-methyl-1,4-diaminobenzene, 2,6-dimethyl-1,4-diaminobenzene, 2,5-dimethyl-1,4-diaminobenzene, 2,3-dimethyl-1,4-diaminobenzene, 2-chloro-1,4-diaminobenzene, 2-methoxy-1,4-diaminobenzene, 1-phenylamino-4-aminobenzene, 1-dimethylamino-4-aminobenzene, 1-diethylamino-4-aminooenzene, 1-bis($\beta$-hydroxyethyl)amino-4-aminobenzene, 1-methoxyethylamino-4-aminobenzene, 2-hydroxymethyl-1,4-diaminoenzene, 2-hydroxyethyl-1,4-diaminobenzene, 2-isopropyl-1,4-diaminobenzene, 1-hydroxypropyl . . . 4-aminobenzene, 2,6-dimethyl-3-methoxy-1,4-diaminobenzene, 1-amino-4-hydroxybenzene and its derivatives substituted on the benzene ring such as 2-methyl-1-amino-4-hydroxybenzene, 1-methylamino-4-hydroxybenzene and hydroquinone; 2,5-diaminopyridine and its N-substituted derivatives substituted at position 2 with alkyl and hydroxyalkyl groups; 1-amino-2-hydroxybenzene, 6-methyl-1-hydroxy-2-aminobenzene, 4-methyl-1-amino-2-hydroxybenzene and 2,4,5,6-tetraaminopyridine and the N-substituted derivatives such as those substituted, for example, with an alkyl or hydroxyalkyl group, and the like.

The dyeing compositions according to the invention can also contain one or more modifiers or couplers, also known as meta derivatives. There may be mentioned, more especially, phenols, meta-diphenols, meta-aminophenols and meta-phenylenediamines, these compounds optionally being able to be substituted on the amino groups, on the phenol groups or on the benzene ring with alkyl, alkoxy, hydroxyalkyl and alkylamino groups, and the like.

It is also possible to use as couplers mono- or dihydroxylated derivatives of naphthalene, as well as heterocyclic compounds such as pyrazolones or diketo compounds. These derivatives can also be substituted with alkyl, hydroxyalkyl or halogen groups on the non-monovalent radicals as well as on the aromatic and heterocyclic rings.

Among these couplers, there may be mentioned, more especially, 3,4-methylenedioxyphenol, 3,4-methylenedioxy-1-[($\beta$-hydroxyethyl)amino]benzene, 1-methoxy-2-amino-4-[($\beta$-hydroxyethyl)amino]benzene, 1-hydroxy-3-(dimethylamino)benzene, 6-methyl-1-hydroxy-3-aminobenzene, 6-methyl-1-hydroxy-3[($\beta$-hydroxyethyl)amino]benzene, 2,4-dichloro-1-hydroxy-3-aminobenzene, 4,6-dichloro-1-hydroxy-3-aminobenzene, 1-hydroxy-3-(diethylamino)benzene, 1-hydroxy-2-methyl-3-aminobenzene, 2-chloro-6-methyl-1-hydroxy-3-aminobenzene, 1,3-diaminobenzene, 6-methoxy-1,3-diaminobenzene, 6-hydroxyethyloxy-1,3-diaminobenzene, 6-methoxy-5-ethyl-1,3-diaminobenzene, 6-ethyloxy-1,3-diaminibenzene, 1-bis($\beta$-hydroxyethyl)amino-3-aminobenzene, 2-methyl-1,3-diaminobenzene, 6-methoxy-1-amino-3-[($\beta$-hydroxyethyl)amino]benzene, 6-($\beta$-aminoethyloxy)-1,3-diaminobenzene, 6-($\beta$-hydroxyethyloxy)-1-amino-3-(methylamino)benzene, 6-carboxymethyloxy-1,3-diaminobenzene, 6-ethyloxy-1-bis($\beta$-hydroxyethyl)amino-3-aminobenzene, 6-hydroxyethyl-1,3-diaminobenzene, 1-hydroxy-2-isopropyl-5-methylbenzene, 1,3-dihydroxybenzene, 2-chloro-1,3-dihydroxybenzene, 2-methyl-1,3-dihydroxybenzene, 4-chloro-1,3-dihydroxybenzene, 5,6-dichloro-2-methyl-1,3-dihydroxybenzene, 1-hydroxy-3-aminobenzene, 1-hydroxy-3-(carbamoylmethylamino)benzene, 2,7-dihydroxynaphthalene, 2,3-dihydroxynaphthalene, 6-hydroxybenzomorpholine, 4-methyl-2,6-dihydroxypyridine, 2,6-dihydroxypyridine, 2,6-diaminopyridine, 6-aminobenzomorpholine, 1-phenyl-3-methyl-5-pyrazolone, 1-hydroxynaphthalene, 1,7-dihydroxynaphthalene and 1,5-dihydroxynaphthalene.

The bio-heteropolysaccharides used according to the invention are synthesized by fermentation of sugars by microorganisms. The bio-heteropolysaccharides contain, in particular, mannose, glucose, glucoronic acid or galacturonic acid units in their chain.

They can comprise, more especially, the xanthan gums produced by the bacterium *Xanthomonas campestri* and the mutants and variants of the latter.

The xanthan gums have a viscosity of between 600 and 1,650 cP for an aqueous composition containing 1% of xanthan gum (measured in a Brookfield type LVT viscometer at 60 rpm) and have a molecular weight of between 1,000,000 and 50,000,000.

The xanthan gums incorporate in their structure 3 different monosaccharides, namely mannose, glucose and glucuronic acid in salt form.

Products of this kind are, more especially, marketed under the name KELTROL by KELCO, a 1% strength aqueous solution of which has a Brookfield LVT viscosity at 60 rpm of 1,200 to 1,600 cP, KELZAN S marketed by KELCO, a 1% strength aqueous solution of which has a Brookfield LVT viscosity at 60 rpm of 850 cP, RHODOPOL 23, 23 U and 23 C marketed by RHONE-POULENC, a 0.3% strength aqueous solution of which has a Brookfield LVT viscosity at 30 rpm of 450±50 cP, RHODIGEL 23 sold by RHONE-POULENC, DEUTERON XG marketed by SCHONER GmbH, the viscosity of a 1% strength aqueous solution of which is 1,200 cP measured in a Brookfield LVT viscometer at 30 rpm, ACTIGUM CX9 marketed by CECA having a viscosity of 1,200 cP measured in a Brookfield LVT viscometer at 30 rpm for a 1% strength aqueous solution; KELZAN K9 C57, the viscosity of a 1% strength aqueous solution of which is 630 to 1,000 cP measured in a Brookfield LVS viscometer at 60 rpm, marketed by KELCO; KELZAN K8 B12, the Haake Rotovisco RVI, MVI viscosity of which at 25° C. is 1,000 cP at 10 s$^{-1}$, marketed by KELCO; and KELZAN K3 B130, marketed by KELCO.

The heteropolysaccharides can also be chosen from the following:

(a) The biopolymer PS 87 produced by the bacterium *Bacillus polymyxa*, which incorporates glucose, galactose, mannose, fucose and glucuronic acid in its structure; this biopolymer PS 87 is described in European Patent Application No. 23,397;

(b) The biopolymer S88 produced by PSEUDOMONAS strain ATCC 31554, which incorporates rhamnose, glucose, mannose and glucuronic acid in its structure; this biopolymer is described in British Patent 2,058,106;

(c) The biopolymer S130 produced by ALCALIGENES strain ATCC 31555, which incorporates rhamnose, glucose, mannose and glucuronic acid in its molecules; this biopolymer is described in British Patent 2,058,107;

(d) The biopolymer S139 produced by PSEUDOMONAS strain ATCC 31644, which incorporates rhamnose, glucose, mannose, galactose and galacturonic acid in its molecules; this biopolymer is described in U.S. Pat. No. 4,454,316;

(e) The biopolymer S198 produced by ALCALIGENES strain ATCC 31853, which incorporates rhamnose, glucose, mannose and glucuronic acid in its molecules; this biopolymer is described in European Patent Application 64,354;

(f) The exocellular biopolymer produced by species of bacteria, yeasts, fungi or gram-positive or -negative algae; this biopolymer is described in West German Patent Application No. 3,224,547.

The oxidation dye precursors are present in the compositions according to the invention in the proportion 0.001 to 10% by weight, and preferably between 0.01 and 5% by weight, relative to the total weight of the composition. The xanthan gum is present in the compositions according to invention in proportions of between 0.1 and 5%, and preferably between 0.5 and 3%, by weight relative to the total weight of the composition.

The compositions according to the invention can contain direct dyes such as azo and anthraquinone dyes, or nitro dyes of the benzene series, for the purpose of enriching or modifying the shade of the colorations obtained using the combinations of oxidation dye precursors. These direct dyeing agents are present in the proportion of between 0.01 and 5% by weight relative to the total weight of the composition.

The compositions can also contain anionic, cationic, non-ionic or amphoteric surfactants, or mixtures thereof. Among these preferred surfactants, there may be mentioned soaps, alkyle benzenesulphonates, alkyle naphthalenesulphonates, quaternary ammonium salts, fatty acid diethanolamides, and polyoxyethylenated or polyglycerolated acids, alcohols or amides.

The surfactants are present in the compositions according to the invention in proportions of between 0.1 and 55% by weight, and preferably between 1 and 40% by weight, relative to the total weight of the composition.

The compositions can also contain solvents in proportions sufficient to enable the dye precursors, as used, to dissolve. Among these solvents, there may be mentioned water or mixtures of water and solvents such as lower alcohols, for example ethanol or isopropanol, glycerol, glycols or glycol ethers such as ethylene glycol monobutyl ether and propylene glycol monobutyl ether, diethylene glycol monoethyl ether and monomethyl ether, and the like.

These solvents are preferably used in proportions of 1 to 50% by weight, and more especially from 3 to 30% by weight, relative to the total weight of the composition.

These compositions can also contain anionic, nonionic, cationic or amphoteric polymers, or mixtures thereof, in proportions ranging from 0.1 to 5% by weight.

These compositions can also contain adjuvants customarily used in hair dyeing compositions, such as penetrants, sequestering agents, buffers, perfumes, preservatives, reducing agents or antioxidants.

The pH of the compositions can be adjusted to values between 8 and 11.5 with alkalinizing agents such as ammonia solution, alkanolamines such as monoethanolamine, diethanolamine and triethanolamine, ammonium carbonate, potassium carbonate and sodium carbonate, sodium hydroxide and 2-amino-2-methyl-1-propanol, or acidifying agents.

The compositions according to the invention take the form of a liquid which has been thickened to a greater or lesser extent, a gel or a cream which holds its position well on the hair.

The bio-heteropolysaccharides, and especially xanthan gum, in addition to their properties indicated above, also perform the role of thickener and have the effect of holding the dyeing composition in position on the hair.

The compositions according to the invention which do not contain an oxidizing agent are mixed at the time of use with compositions containing an oxidizing agent which develops the coloration. This agent can be hydrogen peroxide, urea or a persalt.

When ready for use, the composition is then applied on the hair with an exposure time which varies from 2 minutes to 1 hour, and is preferably, for example, from 5 to 30 minutes. The hair is rinsed, optionally washed with shampoo, rinsed again and dried.

The examples which follow are intended to illustrate the invention without being in any way limitative in nature.

EXAMPLE 1

The following dyeing composition is prepared:

| | |
|---|---|
| p-phenylenediamine | 1 g |
| p-aminophenol | 2.95 g |
| N—methyl-p-aminophenol | 2.14 g |
| o-aminophenol | 0.30 g |
| resorcinol | 0.79 g |
| m-aminophenol | 0.60 g |
| 6-hydroxyethyloxy-1,3-diaminobenzene | 0.78 g |
| 1-hydroxy-6-methyl-3-[(β-hydroxyethyl)amino]benzene | 3 g |
| sodium alkyl ether sulphate | 5.6 g |
| xanthan gum, sold under the name KELTROL by KELCO | 2 g |
| diethanolamides of coconut fatty acids | 3.5 g |
| glycol distearate | 2 g |
| ammonium thiolactate | 0.8 g |
| diethylenetriaminepentaacetic acid pentasodium salt | 2 g |
| ammonia solution containing 20% of $NH_3$ | 12.9 g |
| perfume, preservative qs | |
| water qs | 100 g |

At the time of use, one part of an oxidizing milk containing $H_2O_2$ equivalent to "20 volumes" is added to an equal part by weight of this composition.

When applied for 30 minutes at room temperature on natural hair which is 90% white, and may or may not be permanently-waved, this mixtures endows it, after rinsing and shampooing, with a coppery dark blond coloration.

EXAMPLE 2

The following composition is prepared:

| | |
|---|---|
| 2-methyl-1,4-diaminobenzene | 0.7 g |
| p-aminophenol | 0.8 g |
| N—methyl-p-aminophenol hemisulphate | 0.35 g |
| resorcinol | 0.20 g |
| m-aminophenol | 0.12 g |
| 2,4-(diaminophenoxy)ethanol dihydrochloride | 0.30 g |
| 1-methyl-2-hydroxy-4-[(β-hydroxyethyl)amino]benzene | 0.16 g |
| lauric diethanolamide | 3 g |
| xanthan gum, sold by RHONE-POULENC under the name RHODOPOL 23 U | 2.5 g |
| ammonia solution containing 20% of $NH_3$ | 12 g |
| thiolactic acid | 0.3 g |
| water qs | 100 g |

At the time of use, this gelified liquid composition is diluted with its own weight of "20 volumes" hydrogen peroxide. The mixture is applied on brown hair for 30 minutes.

After being rinsed, washed with shampoo and dried, the hair possesses a purple-violet chestnut coloration.

EXAMPLE 3

The following composition is prepared:

| | |
|---|---|
| p-phenylenediamine | 0.3 g |
| p-aminophenol | 0.9 g |
| 1-methyl-2-hydroxy-4-[(β-hydroxyethyl)-amino]benzene | 0.5 g |
| 2,4-(diaminophenoxy)ethanol dihydrochloride | 0.2 g |
| xanthan gum, sold by KELCO under the name KELTROL | 1.8 g |
| sodium alkyl ether sulphate containing 28% AM, sold under the name SACTIPON 8533 by LEVER | 20 g |
| lauric diethanolamide | 3 g |
| ammonia solution containing 20% of $NH_3$ | 13 g |
| ethylenediaminetetraacetic acid | 0.1 g |
| thiolactic acid | 0.3 g |
| water qs | 100 g |

This composition is mixed with an equal weight of "20 volumes" hydrogen peroxide, and the product obtained is applied for 30 minutes on brown hair.

After being rinsed, washed with shampoo and dried, the hair is coloured in a reddish brown chestnut shade.

EXAMPLE 4

The following composition is prepared:

| | |
|---|---|
| 2-methyl-1,4-diaminobenzene | 0.8 g |
| p-aminophenol | 0.05 g |
| 1-methyl-2-hydroxy-4-[(β-hydroxyethyl)-amino]benzene | 0.95 g |
| m-aminophenol | 0.3 g |
| xanthan gum, sold by KELCO under the name KELTROL | 2.2 g |
| sodium alkyl ether sulphate containing 28% AM, sold under the name SACTIPON 8533 by LEVER | 20 g |
| oleic diethanolamide | 2.5 g |
| ethylenediaminetetraacetic acid | 0.1 g |
| thiolactic acid | 0.3 g |
| ammonia solution containing 20% of NH$_3$ | 12 g |
| water qs | 100 g |

This gelified composition is diluted at the time of use with an equal weight of "20 volumes" H$_2$O$_2$. The mixture obtained is applied for 30 minutes on brown hair.

After the hair is rinsed, washed with shampoo and dried, a golden chestnut shade is obtained.

I claim:

1. In combination,
   (A) a dyeing composition for keratinous fibres and especially for human hair, said dyeing composition being intended to be mixed at the time of use with an oxidation composition containing an oxidizing agent, containing 0.001 to 10% by weight of at least one oxidation dye precursor relative to the total weight of the dyeing composition and 0.1 to 5% by weight of at least one water-soluble bio-heteropolysaccharide, relative to the total weight of the dyeing composition in a cosmetically acceptable medium, with the proviso that the dyeing composition does not contain an oxidizing agent which develops the at least one oxidation dye precursor, the said bio-heteropolysaccharide being a xanthan gum having a viscosity of between 850 and 1,650 cP for an aqueous composition containing 1% of xanthan gum, measured in a Brookfield LVT viscometer at 60 rpm and a molecular weight of between 1,000,000 and 50,000,000; and
   (B) an oxidation composition containing an oxidizing agent which develops the at least one oxidation dye precursor of the dyeing composition.

2. Composition according to claim 1, wherein the oxidation dye precursor is an oxidation dye precursor of the para or ortho type, selected from the group consisting of para-phenylenediamines, para-aminophenols, para-diphenols, ortho-aminophenols, ortho-phenylenediamines, ortho-diphenols and pyridine or pyrimidine derivatives.

3. Composition according to claim 1 containing also modifiers or couplers selected from the group consisting of phenols, meta-diphenols, meta-aminophenols, meta-phenylenediamines, mono- or dihydroxylated derivatives of naphthalene, pyrazolones and diketo compounds.

4. Composition according to claim 1, wherein the oxidation dye precursor is of the para or ortho type and is selected from the group consisting of p-phenylenediamine, 2-methyl-1,4-diaminobenzene, 2,6-dimethyl-1,4-diaminobenzene, 2,5-dimethyl-1,4-diaminobenzene, 2,3-dimethyl-1,4-diaminobenzene, 2-chloro-1,4-diaminobenzene, 2-methoxy-1,4-diaminobenzene, 1-phenylamino-4-aminobenzene, 1-dimethyl amino-4-aminobenzene, 1-diethylamino-4-aminobenzene, 1-bis(β-hydroxyethyl)amino-4-aminobenzene, 1-methoxyethylamino-4-aminobenzene, 2-hydroxymethyl-1,4-diaminobenzene, 2-hydroxyethyl-1,4-diaminobenzene, 2-isopropyl-1,4-diaminobenzene, 1-hydroxypropyl-4-aminobenzene, 2,6-dimethyl-3-methoxy-1,4-diaminobenzene, 1-amino-4-hydroxybenzene, 2-methyl-1-amino-4-hydroxybenzene, 1-methylamino-4-hydroxybenzene and hydroquinone, 2,5-diaminopyridine and its N-substituted derivatives substituted at position 2, 1-amino-2-hydroxybenzene, 6-methyl-1-hydroxy-2-aminobenzene, 4-methyl-1-amino-2-hydroxybenzene and 2,4,5,6-tetraamino-pyridine.

5. Composition according to claim 3, wherein the coupler or modifier is selected from the group consisting of 3,4-methylenedioxyphenol, 3,4-methylenedioxy-1-[(β-hydroxyethyl)amino]benzene, 1-methoxy-2-amino-4-[(β-hydroxyethyl)amino]benzene, 1-hydroxy-3-(dimethylamino)benzene, 6-methyl-1-hydroxy-3-aminobenzene, 6-methyl-1-hydroxy-3[(β-hydroxyethyl)amino]benzene, 2,4-dichloro-1-hydroxy-3-aminobenzene, 4,6-dichloro-1-hydroxy-3-aminobenzene, 1-hydroxy-3-(diethylamino)benzene, 1-hydroxy-2-methyl-3-aminobenzene, 2-chloro-6-methyl-1-hydroxy-3-aminobenzene, 1,3-diaminobenzene, 6-methoxy-1,3-diaminobenzene, 6-hydroxyethyloxy-1,3-diaminobenzene, 6-methoxy-5-ethyl-1,3-diaminobenzene, 6-ethyloxy-1,3-diaminobenzene, 1-bis(β-hydroxyethyl)amino-3-aminobenzene, 2-methyl-1,3-diaminobenzene, 6-methoxy-1-amino-3-[(β-hydroxyethyl)amino]benzene, 6-(β-aminoethyloxy)-1,3-diaminobenzene, 6-(β-hydroxyethyloxy)-1-amino-3-(methylamino)benzene, 6-carboxymethyloxy-1,3-diaminobenzene, 6-ethyloxy-1-bis(β-hydroxyethyl)amino-3-aminobenzene, 6-hydroxyethyl-1,3-diaminobenzene, 1-hydroxy-2-isopropyl-5-methylbenzene, 1,3-dihydroxybenzene, 2-chloro-1,3-dihydroxybenzene, 2-methyl-1,3-dihydroxybenzene, 4-chloro-1,3-dihydroxybenzene, 5,6-dichloro-2-methyl-1,3-dihydroxybenzene, 1-hydroxy-3-aminobenzene, 1-hydroxy-3-(carbamoylmethylamino)benzene, 2,7-dihydroxynaphthalene, 2,3-dihydroxynaphthalene, 6-hydroxybenzomorpholine, 4-methyl-2,6-dihydroxypyridine, 2,6-dihydroxypyridine, 2,6-diaminopyridine, 6-aminobenzomorpholine, 1-phenyl-3-methyl-5-pyrazolone, 1-hydroxynaphthalene, 1,7-dihydroxynaphthalene and 1,5-dihydroxynaphthalene.

6. Composition according to claim 1, containing also direct dyes chosen from azo and anthraquinone dyes and nitro derivatives of the benzene series in proportions of between 0.01 and 5% by weight.

7. Composition according to claim 1, containing also anionic, cationic, non-ionic or amphoteric surfactants, or mixtures thereof, in proportions of 0.1 to 55% by weight.

8. Composition according to claim 1, wherein the cosmetically acceptable medium consists of water or a mixture of water and solvents chosen from lower alcohols, glycols or glycol ethers.

9. Composition according to claim 1, containing also anionic, cationic, non-ionic or amphoteric polymers, or mixtures thereof, in proportions of 0.1 to 5% by weight.

10. Composition according to claim 1, having a pH of between 8 and 11.5.

11. Composition according to claim 1, containing also penetrants, sequestering agents, buffers, perfumes, preservatives, reducing agents or antioxidants.

12. A process for dyeing keratinous fibres and especially human hair comprising mixing the dyeing composition and oxidation composition of claim 1 at the time of use and applying the mixed compositions to said keratinous fibres for a time sufficient to effect dyeing of said keratinous fibres.

* * * * *